(12) United States Patent
Sobol

(10) Patent No.: US 10,168,430 B2
(45) Date of Patent: Jan. 1, 2019

(54) WIRELESS DEVICES AND SYSTEMS FOR TRACKING PATIENTS AND METHODS FOR USING THE LIKE

(71) Applicant: Adam Sobol, Dayton, OH (US)

(72) Inventor: Adam Sobol, Dayton, OH (US)

( * ) Notice: Subject to any disclaimer, the term of this patent is extended or adjusted under 35 U.S.C. 154(b) by 437 days.

(21) Appl. No.: 14/941,025

(22) Filed: Nov. 13, 2015

(65) Prior Publication Data

US 2016/0139273 A1 May 19, 2016

Related U.S. Application Data

(60) Provisional application No. 62/123,440, filed on Nov. 17, 2014.

(51) Int. Cl.

| | |
|---|---|
| *G01S 19/14* | (2010.01) |
| *G01S 19/31* | (2010.01) |
| *A61B 5/0205* | (2006.01) |
| *A61B 5/00* | (2006.01) |
| *H04W 4/80* | (2018.01) |
| *A61B 5/11* | (2006.01) |
| *G01S 19/16* | (2010.01) |

(52) U.S. Cl.
CPC .......... *G01S 19/14* (2013.01); *A61B 5/02055* (2013.01); *A61B 5/1112* (2013.01); *A61B 5/746* (2013.01); *G01S 19/16* (2013.01); *H04W 4/80* (2018.02); *A61B 5/681* (2013.01); *A61B 5/7455* (2013.01); *A61B 2560/0242* (2013.01); *A61B 2562/0204* (2013.01); *A61B 2562/0219* (2013.01)

(58) Field of Classification Search
CPC ......... G01S 19/14; G01S 19/34; H04W 4/008

USPC ........... 342/357.52, 357.65, 357.71, 357.74; 701/468, 519

See application file for complete search history.

(56) References Cited

U.S. PATENT DOCUMENTS

| | | | |
|---|---|---|---|
| 8,868,254 B2 | 10/2014 | Louboutin | |
| 2009/0040041 A1 | 2/2009 | Janetis et al. | |
| 2014/0239065 A1 | 8/2014 | Zhou et al. | |
| 2015/0048942 A1 | 2/2015 | Bertagna et al. | |
| 2015/0112158 A1 | 4/2015 | He | |
| 2016/0021506 A1* | 1/2016 | Bonge, Jr. ............ | A01K 27/009 717/173 |

(Continued)

FOREIGN PATENT DOCUMENTS

CN 103871197 6/2014

*Primary Examiner* — Dao L Phan
(74) *Attorney, Agent, or Firm* — Indiana University Maurer School of Law IP Legal Clinic

(57) ABSTRACT

Disclosed are apparatuses, systems, and methods for tracking patients that suffer from dementia. The disclosed apparatus is a wearable device capable of micro-tracking through Bluetooth Low Energy technology and capable of macro-tracking through GPS technology. The device may additionally include sensors to monitor other information such as the health of the patient or the patient's surrounding environment. The disclosed systems utilize the disclosed device in an overall system for tracking patients. These systems teach how the device interacts with the other components of the system (e.g., signal beacons, wireless transmitters, a central processing unit, mobile computing devices) to provide an integrated system to tracking the location and monitoring the well being of the patient. Finally, methods for tracking patients that use the disclosed devices and systems are disclosed.

20 Claims, 8 Drawing Sheets

(56) References Cited

U.S. PATENT DOCUMENTS

2016/0165853 A1\* 6/2016 Goldfain .............. A01K 29/005
340/573.3

\* cited by examiner

WIRELESS DEVICES AND SYSTEMS FOR TRACKING PATIENTS AND METHODS FOR USING THE LIKE

CROSS-REFERENCE TO RELATED APPLICATIONS

This application claims the benefit of U.S. Provisional Application No. 62/123,440 titled "Wireless Wearable Device Having Care Functionality," to Adam G. Sobol, filed Nov. 17, 2014, the entire disclosure of which is expressly incorporated by reference herein.

FIELD OF THE DISCLOSURE

The present disclosure relates generally to a wearable tracking device for monitoring the location of a wearer. Particularly, it relates to a wearable device that wirelessly communicates information. The disclosure also relates to wireless proximity tracking to track the movement of a wearer of the device, particularly those at risk of wandering, including children or individuals with mental disease such as dementia. The present disclosure also relates to a tracking system utilizing the device and methods for using the device.

BACKGROUND AND BRIEF SUMMARY

Dementia is defined as a decline in mental ability severe enough to interfere with one's daily life. Over five million people suffer from dementia in the United States alone and this number is predicted to increase. Alzheimer's and Parkinson's are common examples of dementia.

One problem in caring for those suffering from dementia is that they may become confused of their surroundings and tend to wander and get lost. If these individuals are not located in a timely manner, they are at risk of injury. To compound the problem, many of the individuals suffering from dementia will not have the mental acuity to remember their name or address even in the event they encounter someone trying to assist them.

The present disclosure is designed to reduce this problem by providing a wearable device designed to track individuals with relation to a predefined geographical area such as one's home or care facility and also one's general location once they are outside of the predefined geographical area. The device is wirelessly connected to a tracking system utilizing macro- and micro-location monitoring technology. The device may also include additional features useful for dementia patients such as the ability to lock and unlock certain doors. Although the device is designed to track patients, it could also be employed for alternative uses. For example, the devices and systems presently disclosed may be used for pets as an alternative to a traditional invisible electronic fence. Another example would be to use the presently disclosed devices and systems for tracking valuable items such as laptop computers, mobile phones, or any other valuable item.

The device can be in the form of a stand-alone device such as wristband, anklet, or it can be imbedded in the patient's clothing or accessories; alternatively, the device can be in a form that clips on to the patient's clothing or accessories. The device includes a power source, a processor, an antenna, a Global Positioning Receiver (GPS) chip, and a Low Energy Bluetooth (BLE) chip. In some embodiments, the device may include additional sensors and equipment to monitor a patient's well-being such as a blood pressure monitor, a heart rate monitor, a gyroscope, an accelerometer, or other sensor that can detect or monitor information related to the patient's health. Some embodiments of the device may also include sensors designed to acquire information about the wearer's environment such as a thermometer, a light sensor, magnetic field detector, or a microphone. The device may also be equipped with notifiers configured to notify the patient of any alert generated by the central processing unit. These notifiers can be in the form of any technology that would catch the attention of the patient so that he or she is aware that the central processing unit has received information that may mean the patient could be in danger. Some exemplary notifiers include vibration motors, LED lights, and an audible speaker.

In addition to the device, the present disclosure teaches a system that may track and monitor the device, log the collected information, send the information to a central processing unit, and generate alerts. The data received by the central processing unit and alerts generated by the central processing unity may be accessed through a user interface that can be displayed on any computing device with Internet access. Another component of the system may be a specified predetermined area in which the patient can move freely. The predetermined area can be set by placing beacons throughout the area in which the patient can move freely, beyond which it may be unsafe or undesirable for the patient to venture without supervision. If the patient wanders outside the predetermined area, a signal is sent to the central processing unit, which then generates a signal or alarm to notify the patient and/or the patient's caregiver. Once outside the predetermined area, the GPS functionality will activate so that the patient can be located.

BRIEF DESCRIPTION OF THE DRAWINGS

The aforementioned aspects and many of the intended advantages of this disclosure will grow to be appreciated at a greater level once references to the following accompanying illustrations are expounded upon.

Equivalent reference components point to corresponding parts throughout the several views. Even though the drawings depict manifestations of components and attributes to the present disclosure, certain features are magnified due to the fact that not only are the drawings not scalable, but also because this method is the best way to illustrate the present disclosure. Wherein, the illustrations depicted are manifestations of the disclosure, and such illustrations shall in no way be interpreted as limiting the scope of the disclosure.

DETAILED DESCRIPTION

Providing adequate care for individuals at risk of wandering poses a unique problem. The present disclosure contemplates devices, systems, and methods for tracking and monitoring patients. The disclosed devices, systems, and methods provide an integrated approach to tracking patients that allows for low energy wireless tracking and monitoring in predetermined areas, such as the patient's residence. Additionally, the disclosed devices, systems, and methods provide an approach to tracking and monitoring patients that have wandered outside of the predetermined area.

Figure 1A:
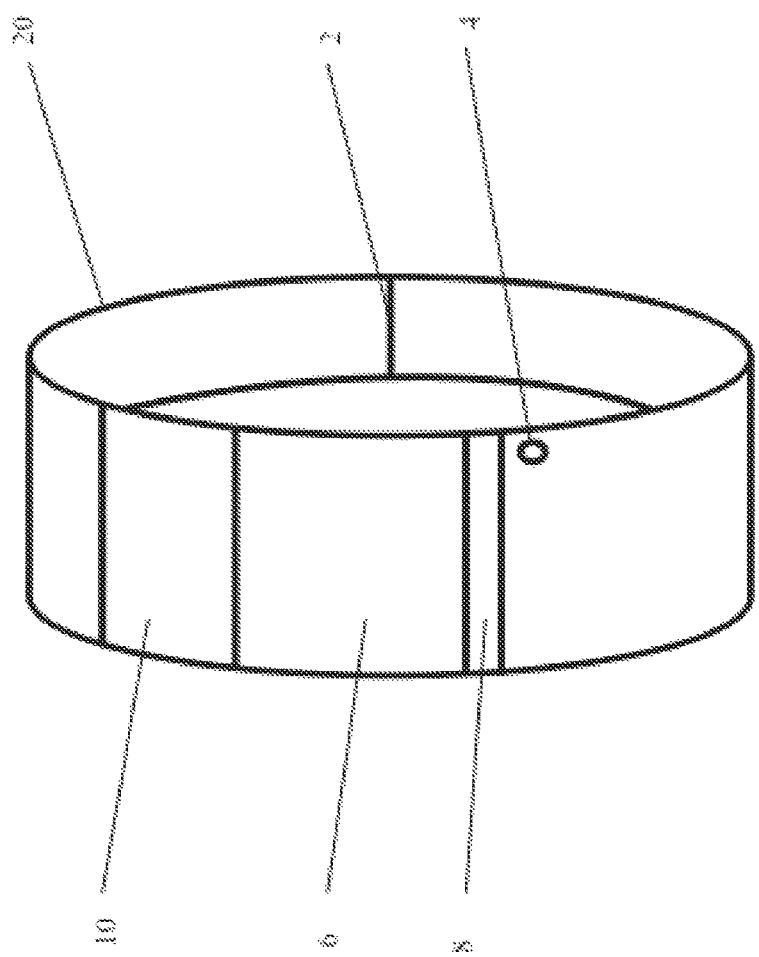
FIG. 1A is a front perspective view of an example of a wearable device in accordance with certain embodiments.
Figure 1B:
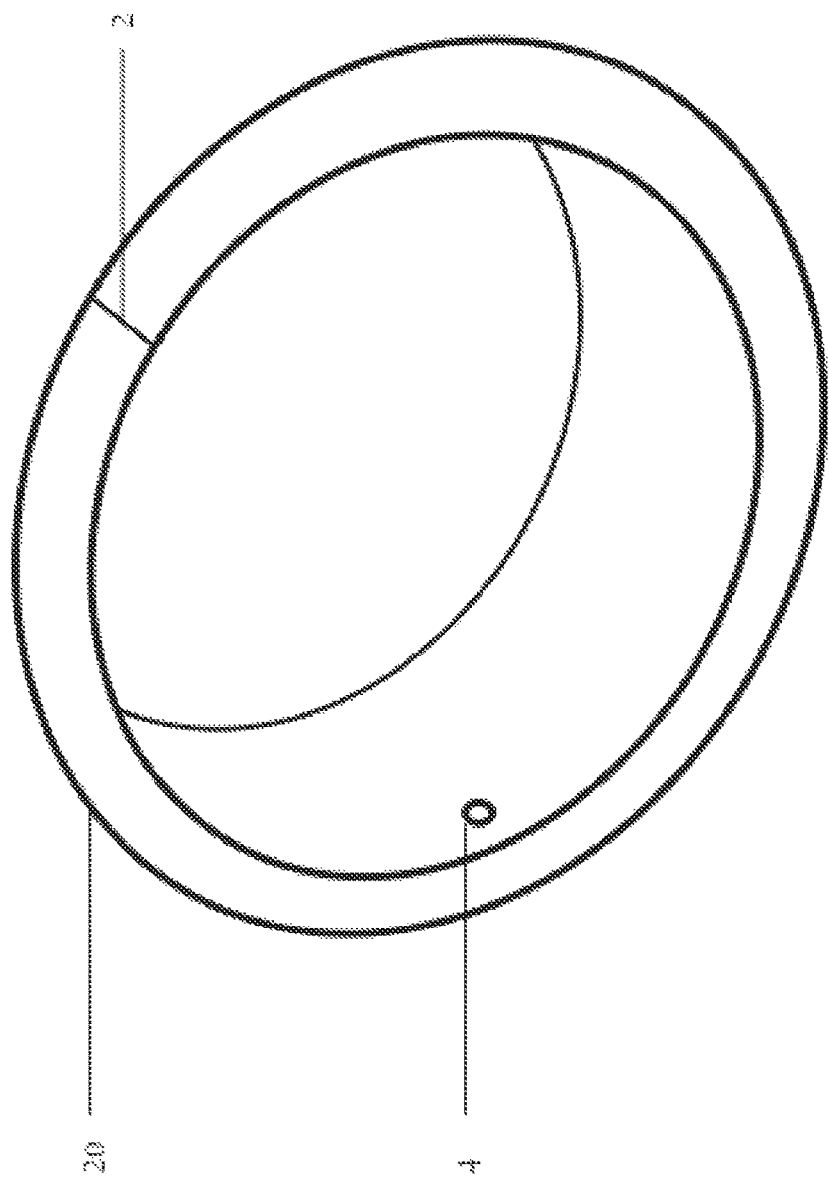
FIG. 1B is a top perspective view of the wearable device of FIG. 1A in accordance with certain embodiments.
Figure 1C:
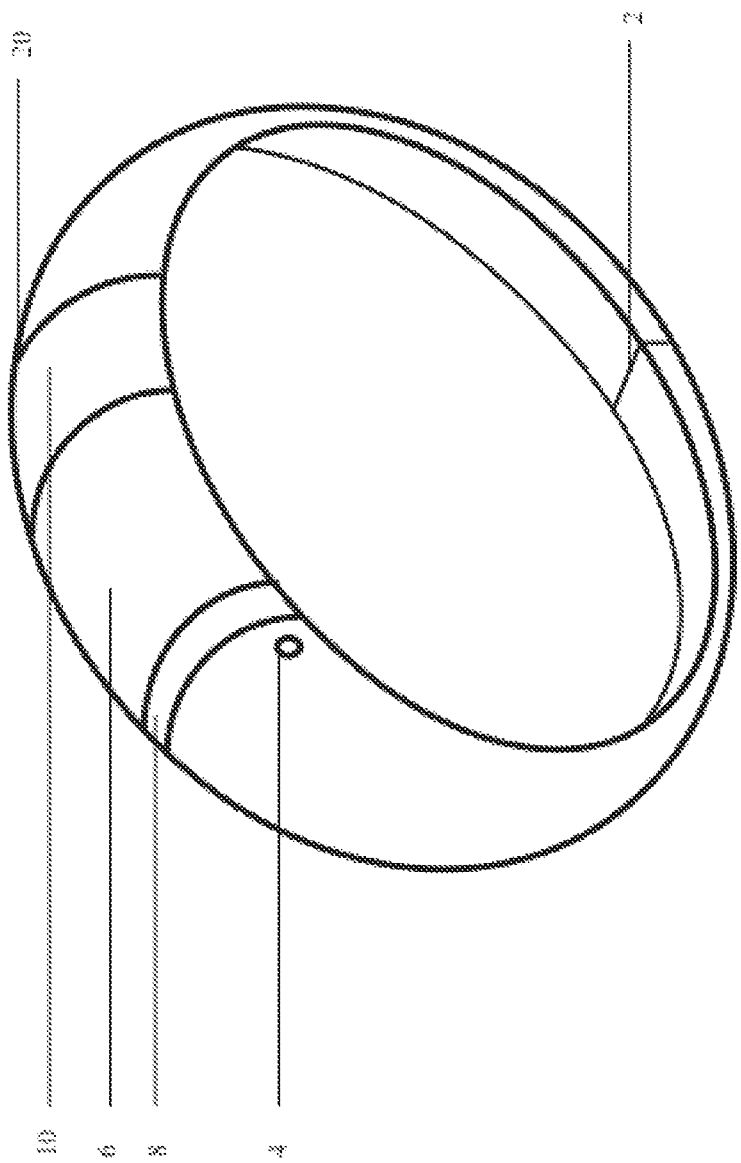
FIG. 1C is a bottom perspective view of the wearable device in accordance with certain embodiments.

Referring to FIGS. 1A-C, an exemplary device 20 is provided. FIG. 1A shows device 20 from the front and FIG. 1B depicts device 20 from the top. In the disclosed embodiment, the form of device 20 is similar to a watch or a bracelet. In alternative embodiments, device 20 may be in the form of an ankle band, a finger ring, a toe ring, a necklace, an earring, glasses, a hearing aid, or any other wearable accessory. In other embodiments, device 20 may be imbedded in the patient's clothing such as a shirt, underwear, shorts, pants, socks, hat, bra, or any other article of clothing. Device 20 may also be in the form of a clip that can be attached to an accessory such as a backpack in certain embodiments.

In some embodiments, device 20 may include a lock 2 that can prevent the patient from removing device 20. Lock 2 may be secured using magnets, RFID technology, a wireless signal, or any other mechanism that allows only a caregiver or authorized personnel to remove device 20. In certain embodiments, device 20 may include a screen 6 capable of displaying information collected by device 20, including any alerts generated. Such information may include, for example, patient's location, information collected by any sensors 4 included in device 20, or information pre-programmed into device 20 such patient's name, address, or health information (e.g., illnesses, allergies, medication). Some embodiments of device 20 may also include a button that allows patient to generate an alert to be sent to a caregiver.

Certain embodiments of device 20 may include sensors 4 on top of device 20 as depicted in FIGS. 1A and 1B. In addition, sensors 4 may also be located on the inside of device 20 as depicted in FIG. 1C. Sensors 4 may be on the inside of device 20 in some embodiments because they may require contact with patient to properly measure patient's health-related information. In some embodiments it may be preferable to place certain sensors 4 on the outside of device 20 as well.

In some embodiments, device 20 may include notifiers 8 that can notify patient that he or she has wandered outside a predetermined area or that data collected by at least one sensor 4 is outside a predetermined threshold meaning patient may be experiencing an adverse health event.

FIGS. 1A and 1C also disclose solar cells 10 that may be present in certain embodiments of device 20. In embodiments where device 20 includes solar cells 10, solar cells 10 would be used as a renewable source of power that would allow device 20 to operate for longer continuous time periods than possible without solar cells 10.

Figure 2:
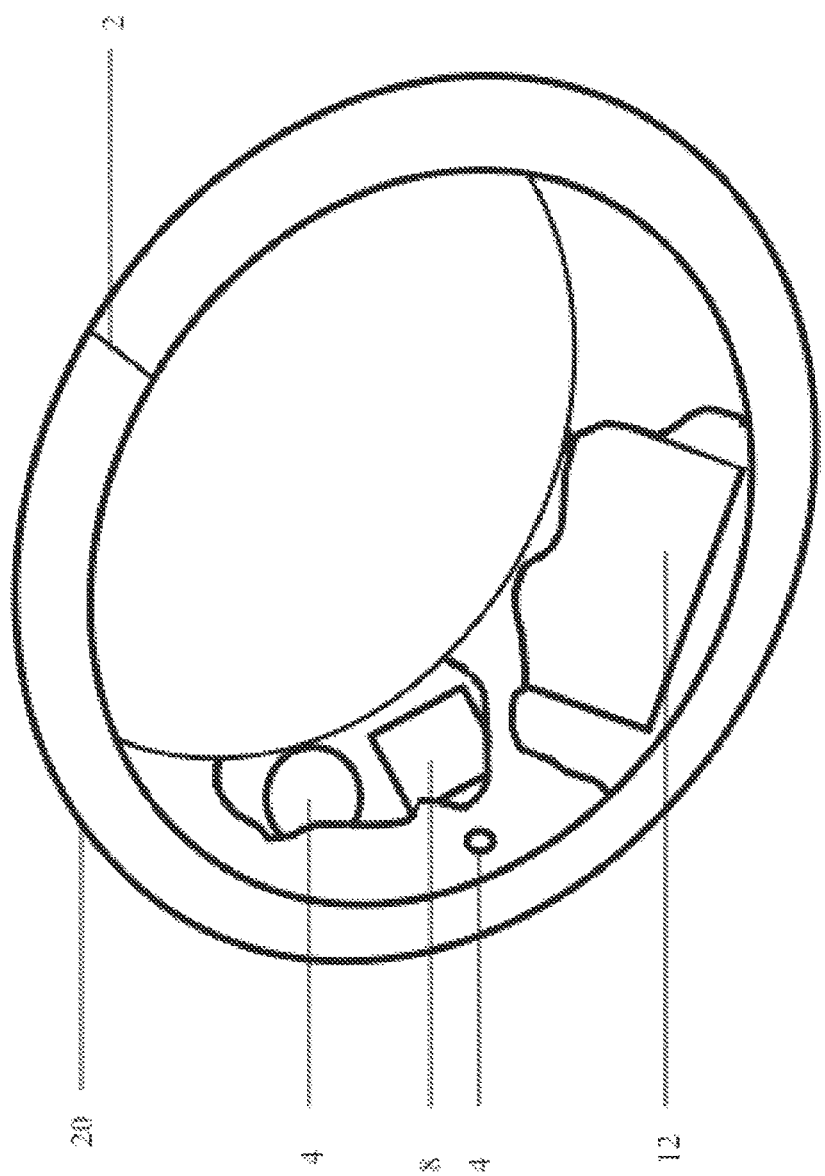
FIG. 2 is a bottom view of the wearable device with a portion cutaway showing the device in accordance with some embodiments to illustrate the interior mechanics.

Referring to FIG. 2, a cutaway view of the bottom of the exemplary device 20 is depicted. FIG. 2 again discloses lock 2 that may be included in some embodiments to prevent the patient from removing device 20. The cutaway view from FIG. 2 demonstrates the location of the interior circuitry 12 as well as interior sensors 4 and notifiers 8 that may be included in certain embodiments of device 20. Some sensors 4 may be advantageously located inside device 20. For example, a gyroscope and/or an accelerometer, which can be used to determine if the patient has fallen, and require no direct contact with the external environment and therefore can be located inside device 20. Similarly, certain notifiers 8 can also be entirely enclosed within device 20. One example of such notifier 8 would be a vibrating electric motor that would cause device 20 to vibrate upon receiving an alert. Device 20 is preferably waterproof or water resistant.

Figure 3:
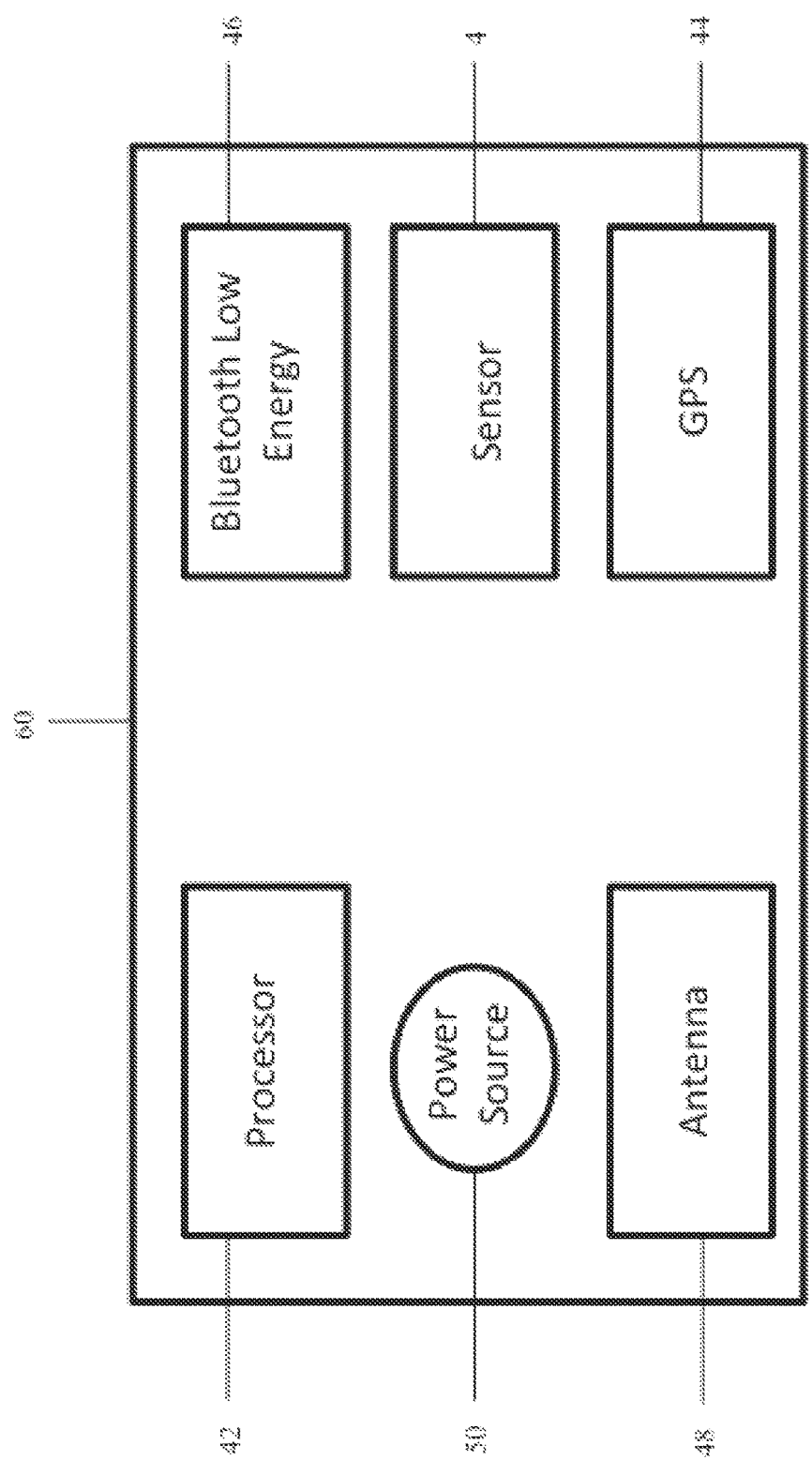
FIG. 3 is a diagrammatic view of a circuit board component of the wearable device of FIG. 1.

Referring now to FIG. 3, a circuit board 60 of device 20 is depicted. Circuit board 60 contains a power source 50, such as a battery, electronically connected to a processor 42. Power source 50 is included to provide electric current to a processor 42 of device 20, a Bluetooth Low Energy (BLE) chip 46, a Global Positioning System (GPS) chip 44, antenna 48, and any other component of device 20 requiring electric power to function. Processor 42 includes logic circuitry that responds to and processes basic instructions. Antenna 48 is communicatively connected to processor 42 and allows device 20 to wirelessly communicate with other devices—such as a cellular phone or computer. According to some embodiments, antenna 48 may include a modem such as a Long Range Radio Frequency (LRRF) modem or a mobile broadband modem. In some embodiments, antenna 48 will transmit signals containing data collected by sensors 4 as well as location information collected by BLE 46 and GPS chip 44. In some embodiments, antenna 48 may also receive information from a wirelessly connected device. One example of a signal that antenna 48 may receive is an alert generated by a central processing unit 94 in systems 100, 120 described herein.

Circuit board 60 also contains BLE chip 46 for microlocation tracking and GPS chip 44 for macro-location tracking. The BLE technology utilizes less energy than GPS technology meaning that regularly utilizing BLE 46 to locate and monitor the patient will allow device 20 to increase the life of power source 50. When device 20 is within an area 68 in which he or she is permitted to roam freely, BLE chip 46 will monitor the patient's movements and transmit them using antenna 48. While in this area 68, BLE chip 46 will also transmit information collected by any sensors 4 and receive any alerts. However, Bluetooth technology may only have a limited range however. Therefore, when the patient wanders outside predetermined area 68, device 20 will switch to location tracking via GPS chip 44. The data collected by GPS chip 44 and any sensors 4 will then be transmitted via antenna 48 by a wireless communication system 92 with a longer range than Bluetooth, such as a cellular phone system. According to the preferred embodiment, GPS chip 44 receives GPS location information (ex. signals used to determine location) from a plurality of satellites. It then calculates the location of device 20 (longitude and latitude) using the GPS location information. This location information is then sent by antenna 48 via wireless communication system 92 to central processing unit 94. According to an alternative embodiment, the raw GPS location information is sent to central processing unit 94 without processing by device 20 and central processing unit 94 calculates the location. Thus, the information received and sent by device 20 may be identical or the information sent by device 20 may be completely or only partially processed.

Figure 4:
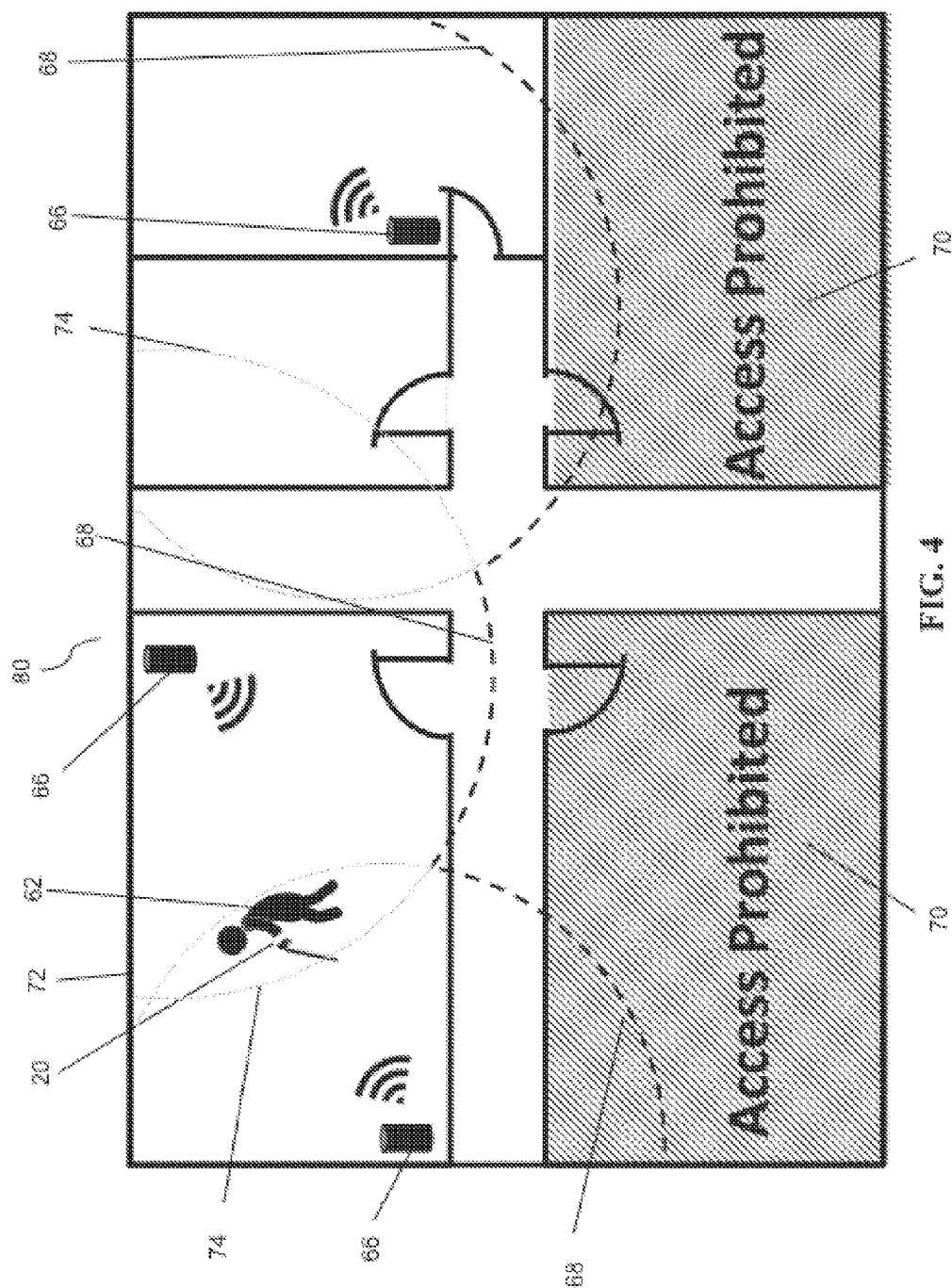
FIG. 4 is a diagrammatic view illustrating a tracking system that operates in a patient's residence using the wearable device of FIG. 1.
Figure 5:
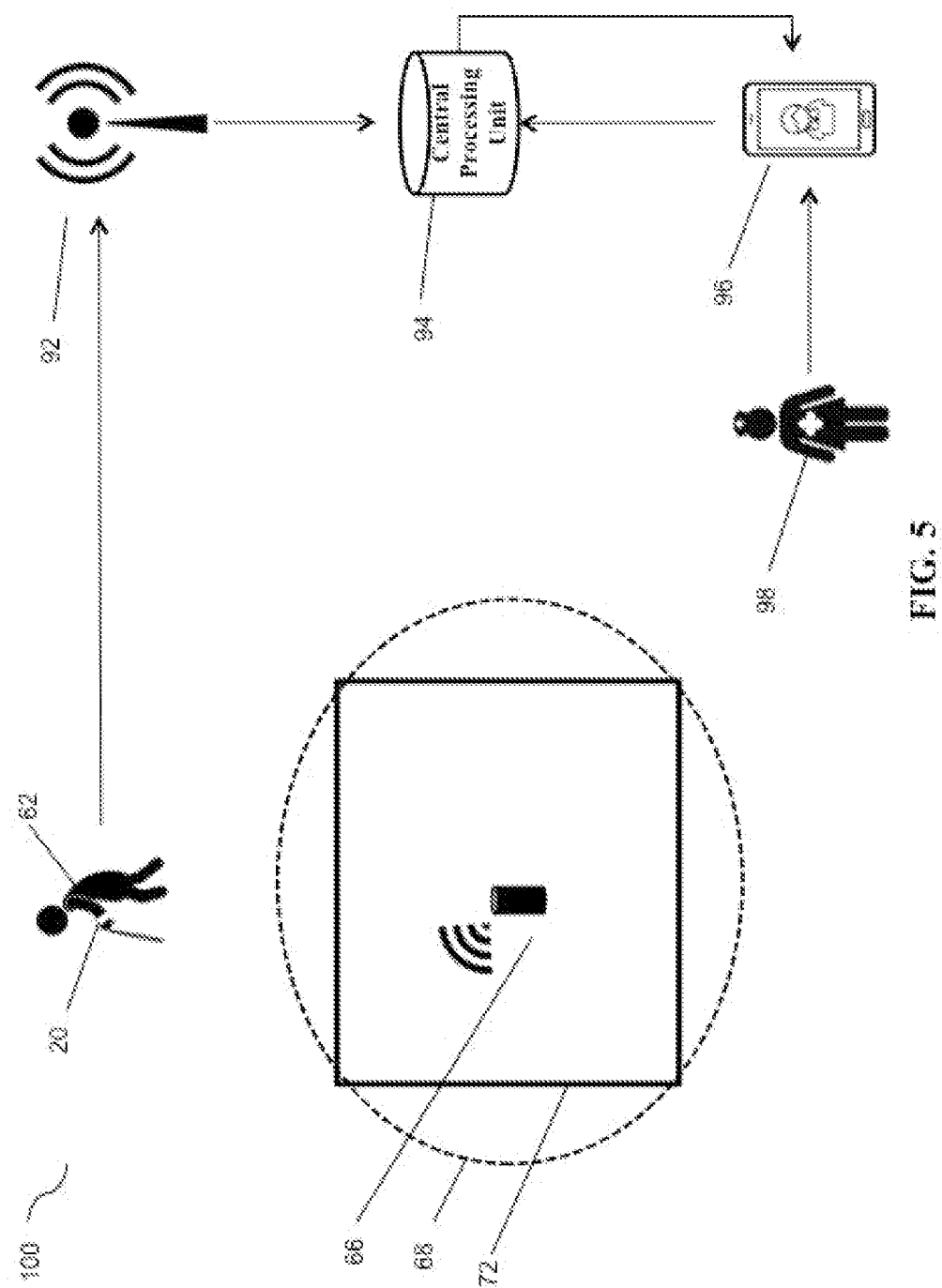
FIG. 5 is a diagrammatic view illustrating the tracking system operating outside of the patient's residence.
Figure 6:
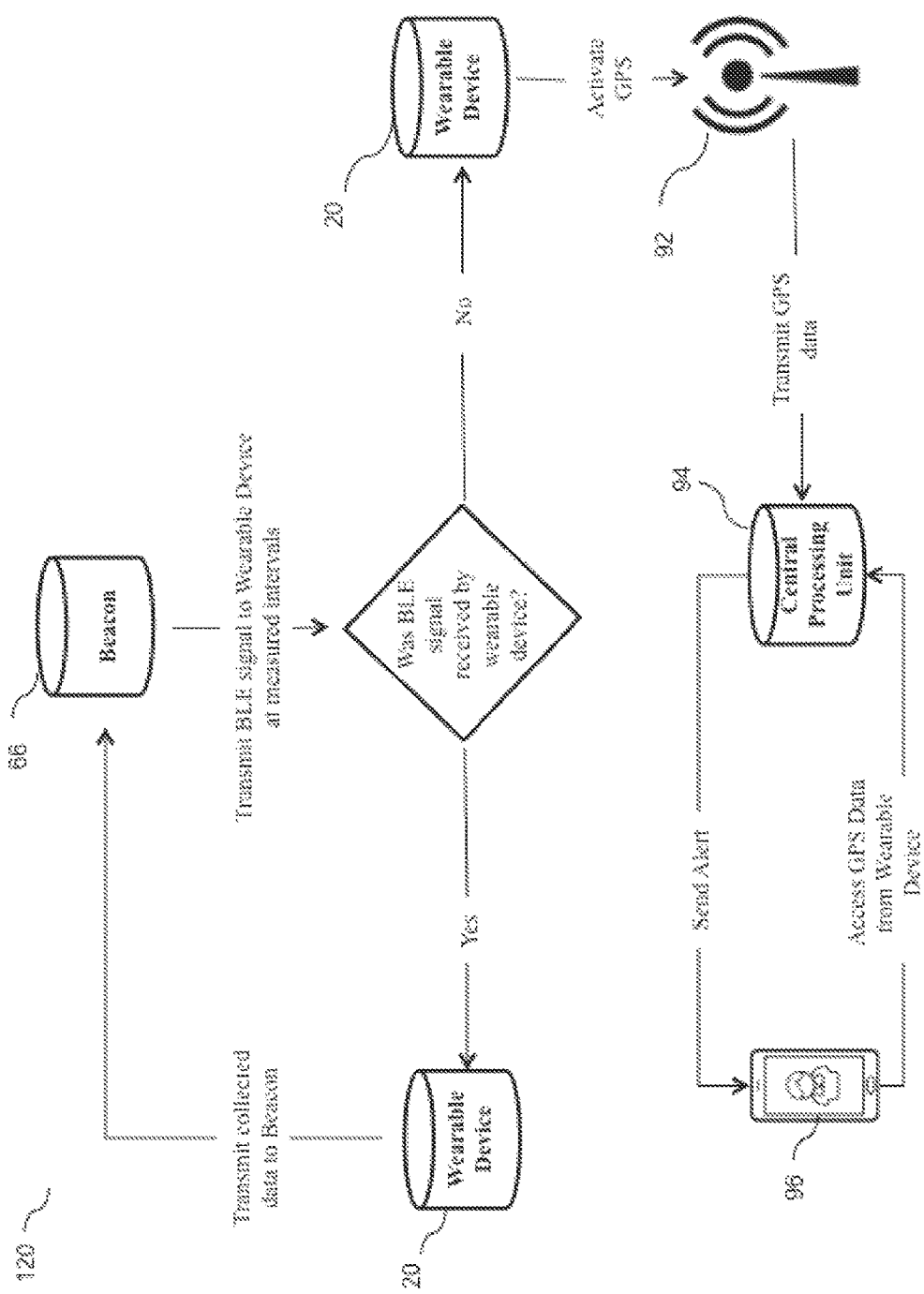
FIG. 6 is a diagrammatic view showing a processes by which the system may operate depending on whether the patient is inside or outside their residence.

Device 20 is intended to track the location of a patient 62. As such, FIGS. 4-6 depict systems 80, 100, 120 for tracking patients 62 wearing device 20. In these embodiments, device 20 should first be activated to be used in system 80, 100, 120. Each device 20 will have a universally unique identifier (UUID) that would allow patient 62 or a caregiver 98 to create an account for patient 62 and associate device 20 with that account using the device's UUID. A central processing unit 94 will store the patient's account information, link collected data to that account, generate alerts based on account preferences, and allow users to view the collected data on any computing device 96 with an internet connection. Central processing unit 94 may consist of a server(s) located offsite from patient 62 and/or a hub located onsite with patient 62. As such, communications between central processing unit 94 and other components (ex. device 20, beacons 66, wireless transmitter 92, etc.) may occur internal to the patient's residence or in and out of the patient's residence using wireless and/or wired communication. Communication between the various components may occur directly between the components or through other components. For example, device 20 may communicate directly with central processing unit 94 or through beacons 66 and/or wireless transmitter 92). According to one embodiment, when central processing unit 94 is located onsite, beacons 66 and/or device 20 may communicate directly with central processing unit 94 in a hub-like manner using wireless and/or wired communication. Beacons 66 may also communicate with other beacons 66 creating a communication chain that ultimately leads to central processing unit 94.

Once device 20 has been registered with an account using the UUID, device 20 is activated. In some embodiments, device 20 may be activated by pairing it (i.e., holding it in close proximity) to a smartphone 96. Once active, device 20 is paired with at least one beacon 66 through a BLE connection.

FIG. 4 discloses one exemplary embodiment of system 80 where patient 62 is inside his or her residence 72. According to this embodiment, inside of his or her residence 72, patient 62 wears device 20 that then interacts with beacons 66 located throughout residence 72. Beacons 66 disclosed as a part of this system 80 may be any device with BLE functionality. In certain embodiments, beacon 66 may be a smartphone, a tablet computer, a desktop computer, a stand-alone device, or any similar electronic device with BLE functionality.

Patient 62 will be virtually restricted to areas in which the patient's caregiver has previously authorized (i.e., predetermined area) 68. According to the disclosed embodiment, once this predetermined area 68 has been set, beacons 66 are placed in locations throughout residence 72 to define predetermined area 68. In certain embodiments, beacons 66 may be programmed so that predetermined range 68 is set as a fixed distance from beacon 66. For example, if the residence 72 is an apartment, beacon 66 may be programmed to set predetermined area 68 to extend in a ten foot radius from beacon 66. If the residence 72 is larger, a house for example, beacon 66 may be programmed to extend in a twenty foot radius from beacon 66. When patient 62 is in predetermined area 68, device 20 would communicate with beacons 66 via BLE. Any area outside that fixed distance from a beacon 66 would be a restricted area 70 that patient 62 would not be permitted to access without caregiver assistance. When patient 62 is in predetermined area 68, device 20 communicates all collected data to beacons 66 at regular intervals. Beacons 66 then transmit this data to a central processing server 94 where the data is then linked to patient's personal account. In alternative embodiments, beacons 66 may not be fixed in location. According to this embodiment, the previously determined area would have to be set electronically (i.e., programmed) rather than proximately.

According to the embodiment disclosed in FIG. 4, if patient 62 wanders outside of predetermined area 68, beacons 66 may generate an alert that warns a caregiver or other party that patient 62 has wandered into a restricted area 70. In certain embodiments, the alert could be delivered directly to a previously identified caregiver as a notification on his or her personal phone, computer, or tablet. Alerts may also be delivered to the caregiver through a text message, an email, or a phone call. In some embodiments, an alert could also be sent to device 20 if patient 62 wanders into a restricted area 70.

Inside predetermined area 68, data collected by beacons 66 is transmitted to a central processing unit and linked to the patient's personal account. When inside of predetermined area 68, a caregiver may monitor patient 62 by accessing the patient's personal account. For example, micro-tracking in predetermined area 68 may be accomplished by measuring the strength of the BLE connection between device 20 and beacon 66. A stronger signal indicates patient 62 is closer to beacon 66, while a weaker signal indicates the opposite. In some embodiments of system 80, multiple beacons 66 may be used. If multiple beacons 66 are programmed to have overlapping ranges, a caregiver may be able to track a patient's location more precisely. For example, FIG. 4 depicts an embodiment of system 80 wherein patient's residence contains three beacons 66. In such an embodiment of system 80, the BLE signal transmitted by multiple beacons 66 creates a signal overlap area 74. Where patient 62 is in a signal overlap area 74, micro-tracking through BLE will become more accurate as the position of patient 62 can be calculated relative to multiple beacons 66.

In alternative embodiments, device 20 may include sensors 4 for monitoring the health information of patient 62 or patient's surrounding environment. According to this embodiment, device 20 may be programmed to monitor data collected by these sensors 4. If this data is outside of a predetermined range (e.g., heart rate or blood pressure exceeds a threshold set by the patient's physician), an alert may be generated that will warn a caregiver. In some embodiments of this system 80, the alerts may also be delivered to device 20.

Referring now to FIG. 5, an exemplary system 100 for tracking patients 62 wearing device 20 when patient 62 wanders outside a predetermined area 68 is disclosed. Some embodiments of system 100 include beacon 66 located in patient's residence 72 that is programmed to set predetermined area 68, outside of which patient 62 is not authorized to roam without the supervision of or permission from a caregiver 98. In some embodiments, if device 20 travels outside of predetermined area 68, beacon 66 will recognize that device 20 is outside predetermined area 68 or, if device 20 is outside range of BLE, beacon 66 will not be able to communicate with device 20. In this embodiment, when device 20 travels outside predetermined area 68, device 20 will continue to monitor the location of patient 62 via GPS instead of BLE. Accordingly, the GPS data is wirelessly transmitted through any wireless signal 92 to central processing unit 94. Wireless signal 92 may be any wireless communication technology including Bluetooth, BLE, RFID, NFC, Zigbee, Z-Wave, Wi-Gi, GSM, CDMA, GPRS, 3G, 4G, WiMax, LTE, Wi-Fi, low power Wi-Fi, Wireless USB, GPS, IPS, LRRF, RF, infrared, satellite communication, or any similar wireless communication technology.

According to this embodiment, once central processing unit 94 receives information indicating that device 20 is outside predetermined area 68, it will generate an alert. The alert may be delivered to any wirelessly connected computing device 96. In alternative embodiments, the alert may also be delivered to device 20. An alert delivered to a wirelessly connected computing device 96 will signal to a caregiver 98 that patient 62 has wandered outside of predetermined area 68. In alternative embodiments, device 20 may also be programmed to monitor data collected by sensors on device 20 and generate an alert when that collected data exceeds a previously determined range.

Referring now to FIG. 6, a process chart for an exemplary system 120 for tracking patients is disclosed. According to this system 120, beacon 66 transmits signals to device 20 at regular intervals. If device 20 is within the range of beacon's BLE transmission, device 20 transmits collected information back to beacon 66. If device 20 does not receive a regular BLE signal from beacon 66, device 20 will activate GPS chip 44 and activate antenna 48 to communicate with a wireless transmitter 92. Wireless transmitter 92 may be configured to transmit and receive any wireless communication technology including Bluetooth, BLE, RFID, LRRF, NFC, Zigbee, Z-Wave, Wi-Gi, GSM, CDMA, GPRS, 3G, 4G, WiMax, LTE, Wi-Fi, low power Wi-Fi, Wireless USB, GPS, LRRF, RF, IPS, infrared, satellite communication, or any similar wireless communication technology.

According to this embodiment of system 120, once device 20 is connected to wireless transmitter 92, device 20 then transmits GPS data wirelessly to central processing unit 94. Central processing unit 94 can then generate an alert sent to any computing device 96 that has an Internet connection. In alternative embodiments, central processing unit 94 may also send alerts to device 20. Any computing device 96 connected to the Internet will be able to pull up a user interface that allows a caregiver or any other person access to a patient's account which may display all the data collected by device 20 that has been transmitted to a beacon 66 or central processing unit 94. Computing device 96 may be a smartphone, a tablet computer, a laptop computer, a desktop computer, or any other computing device capable of accessing the Internet. In certain embodiments of this system 120, the user interface for displaying information collected by device 20 and transmitted to either beacon 66 or central processing unit 94 may be configured to the computing device 20 being utilized. For example, in one embodiment where computing device 96 is a smartphone with the Android mobile operating system, the graphical user interface may be an application built specifically for the Android mobile operating system. In other embodiments, computing device 20 may be running a different operating system (e.g., OS X, Windows, Blackberry. Linux) with a user interface built specifically for that operating system. In other embodiments, the user interface will be web-based so that any device with Internet capabilities may access it.

The invention claimed is:

1. A wearable device for tracking a patient comprising:
   a processor;
   a power source electronically connected to the processor;
   at least one antenna communicatively connected to the processor;
   a Bluetooth Low Energy (BLE) chip communicatively connected to the processor; and
   a Global Positioning System (GPS) chip communicatively connected to the processor;
   the GPS chip being configured to receive GPS location information;
   the at least one antenna being configured to transmit data to at least one signal beacon when the wearable device is inside of a predetermined distance from the at least one beacon, and
   the at least one antenna being configured to transmit information based on the GPS location information when the wearable device is outside of a predetermined distance from the at least one beacon.

2. The wearable device of claim 1, further including at least one sensor to detect health-related information of the patient.

3. The wearable device of claim 2, wherein the at least one sensor includes at least one of a heart rate monitor, a thermometer, an accelerometer, and a gyroscope.

4. The wearable device of claim 1, further including at least one sensor to detect environmental conditions.

5. The wearable device of claim 4, wherein the at least one sensor includes at least one of a thermometer, a light sensor, and a microphone.

6. The wearable device of claim 1, further comprising a lock configured to block removal of the wearable device by the patient.

7. The wearable device of claim 6, wherein the lock is disengaged by at least one of at least one magnet, RFID technology, and a wireless signal.

8. The wearable device of claim 1, further comprising a notifier device configured to notify the patient of any alerts sent wirelessly to the tracking device.

9. The wearable device of claim 8, wherein the notifier is at least one of a light, a speaker, and a vibration motor.

10. A system for tracking patients comprising:
    a wearable tracking device configured to be worn by a patient wirelessly connected to a central processing unit, the device including:
    a processor;
    a power source electronically connected to the processor;
    at least one antenna communicatively connected to the processor;
    a BLE chip communicatively connected to the processor; and
    a GPS receiver communicatively connected to the processor;
    at least one beacon configured to transmit BLE signals to and receive BLE signals from the wearable tracking device within a predetermined range of the at least one beacon and configured to wirelessly transmit data received from the wearable tracking device to the central processing unit; and
    at least one computing device wirelessly configured to be connected to the central processing unit capable of displaying data received by the central processing unit the at least one computing device having a user interface.

11. The system for tracking patients of claim 10, wherein the wearable tracking device is wirelessly connected to the central processing unit.

12. The system for tracking patients of claim 10, wherein the wearable tracking device automatically transmits information collected by the wearable tracking device to the at least one beacon when wirelessly connected to the at least one beacon.

13. The system for tracking patients of claim 10, wherein the GPS receiver is activated by the processor to receive GPS data when the wearable tracking device is outside of the predetermined range of the at least one beacon.

14. The system for tracking patients of claim 10, wherein the wearable tracking device includes at least one sensor to monitor the patient's health information.

15. The system for tracking patients of claim 14, wherein the at least one sensor is at least includes at least one of a heart rate monitor, a thermometer, an accelerometer, or a gyroscope.

16. The system for tracking patients of claim 10, wherein the central processing unit is configured to monitor data collected from at least one of the wearable tracking device and the at least one beacon and generate an alert if the collected data is outside the predetermined range, the alert being delivered to the at least one computing device.

17. The system for tracking patients of claim 16, wherein the antenna is configured to receive the alert from the central processing unit.

18. A method for tracking patients using a wearable tracking device with BLE and GPS capabilities, the method comprising:

securing a wearable tracking device to a patient capable of short-range tracking and long-range tracking;

placing at least one beacon capable of wirelessly connecting to the wearable tracking device in an area where the patient is to be monitored to a predetermined space of movement of the patient;

wirelessly transmitting data collected by the wearable tracking device to the at least one beacon through BLE technology when the wearable tracking device is within the predetermined space;

displaying data that has been transmitted to the central processing unit on a user interface displayable on a computing device wirelessly connected to the central processing unit.

19. The method of claim 17, wherein the short-range tracking utilizes BLE technology.

20. The method of claim 17, wherein the long-range tracking utilizes GPS technology.

* * * * *